(12) United States Patent
Tomlinson

(10) Patent No.: US 7,879,044 B2
(45) Date of Patent: Feb. 1, 2011

(54) ATRAUMATIC CIRCUMCISION DEVICE AND METHOD TO USE SAME

(76) Inventor: David R. Tomlinson, 38 Beech Tree Pl., Wakefield, RI (US) 02879

( * ) Notice: Subject to any disclaimer, the term of this patent is extended or adjusted under 35 U.S.C. 154(b) by 932 days.

(21) Appl. No.: 11/571,120

(22) PCT Filed: Jun. 23, 2005

(86) PCT No.: PCT/US2005/022404

§ 371 (c)(1),
(2), (4) Date: May 14, 2007

(87) PCT Pub. No.: WO2006/012274

PCT Pub. Date: Feb. 2, 2006

(65) Prior Publication Data

US 2008/0021482 A1  Jan. 24, 2008

Related U.S. Application Data

(60) Provisional application No. 60/583,259, filed on Jun. 25, 2004.

(51) Int. Cl.
*A61B 17/32* (2006.01)
*A61B 17/08* (2006.01)
(52) U.S. Cl. .................. 606/118; 606/167; 606/171
(58) Field of Classification Search ................. 606/118, 606/167, 135, 174
See application file for complete search history.

(56) References Cited

U.S. PATENT DOCUMENTS

| | | | |
|---|---|---|---|
| 1,765,319 A | 6/1930 | Williams | |
| 2,296,594 A | 12/1941 | Blais et al. | |
| 2,272,072 A | 2/1942 | Ross | |
| 2,353,647 A | 7/1944 | Carmichael | |
| 2,688,969 A | 9/1954 | Livoti | |
| 3,056,407 A | 10/1962 | Kariher et al. | |
| 3,072,126 A | 1/1963 | Fenton | |
| 3,392,728 A | 7/1968 | Bone et al. | |
| 3,473,533 A | 10/1969 | Freda | |
| 3,757,787 A | 9/1973 | Gottlieb | |
| 5,163,943 A | 11/1992 | Mohiuddin et al. | |
| 5,309,641 A | 5/1994 | Wonderley et al. | |
| 5,797,921 A | 8/1998 | Cimini et al. | |
| 6,193,129 B1 | 2/2001 | Bittner et al. | |
| 6,660,012 B2 | 12/2003 | Lahiji | |
| 6,780,194 B2 | 8/2004 | Freedman et al. | |
| 2006/0058814 A1 | 3/2006 | Gillis | |
| 2006/0122626 A1 | 6/2006 | Duel | |
| 2006/0219753 A1 | 10/2006 | Chiu et al. | |

OTHER PUBLICATIONS

Australian Patent Office communication, mailing date May 8, 2008, Examiner's first report on Australian patent application No. 2005267242.

Canadian Patent Office communications, mailing date May 9, 2008, Examiner's first report on Canadian patent application No. 2,571,934.

(Continued)

*Primary Examiner*—Vy Q. Bui
(74) *Attorney, Agent, or Firm*—Peter J. Borghetti

(57) ABSTRACT

A disposable neonatal circumcision device that secures the foreskin of the penis in a precise location, applies radially circumferential clamping, and delivers a longitudinal circumferential cutting device along the path precisely controlled by the device itself, not the operator, ensuring the incision to the clamped foreskin is made in the precise location, independent of the operator.

13 Claims, 8 Drawing Sheets

OTHER PUBLICATIONS

Canadian Patent Office communications, dated May 13, 2009, Examiner's second report on Canadian patent application No. 2,571,934.

Patent Cooperation Treaty Notification of Transmittal of the International Search Report and the Written Opinion of the International Searching Authority, or the Declaration, mailing date Jan. 25, 2006, PCT international application No. PCT/US05/22404.

Patent Cooperation Treaty Written Opinion of the International Searching Authority, mailing date Jan. 25, 2006, PCT international application No. PCT/US05/22404.

United States Patent and Trademark Office communication, mailing date Jun. 26, 2009, Examiner's first report on U.S. Appl. No. 11/768,808.

United States Patent and Trademark Office communication, mailing date Jul. 10, 2009, Examiner's first report on U.S. Appl. No. 11/768,817.

Step  A  B  C  D  E

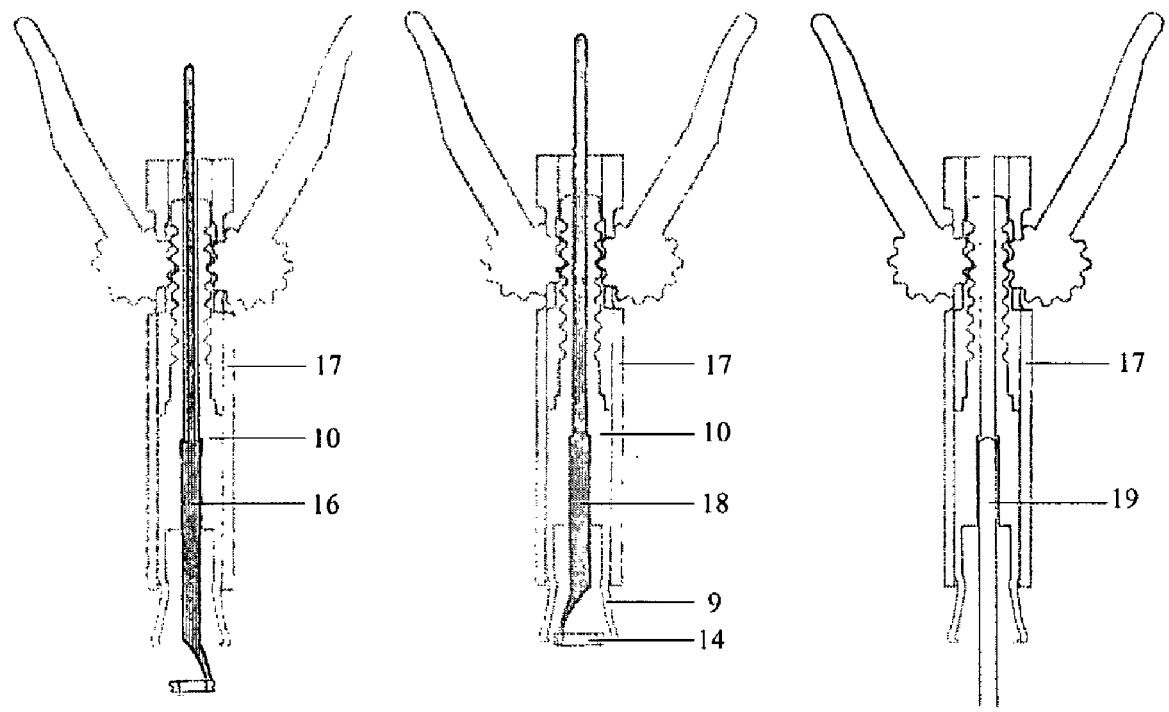
FIG 10    FIG 11    FIG 12
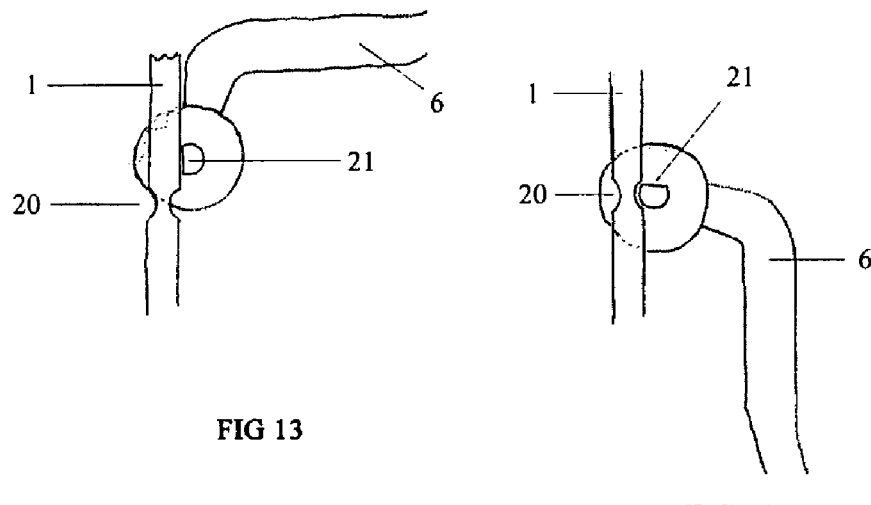
FIG 13
FIG 14

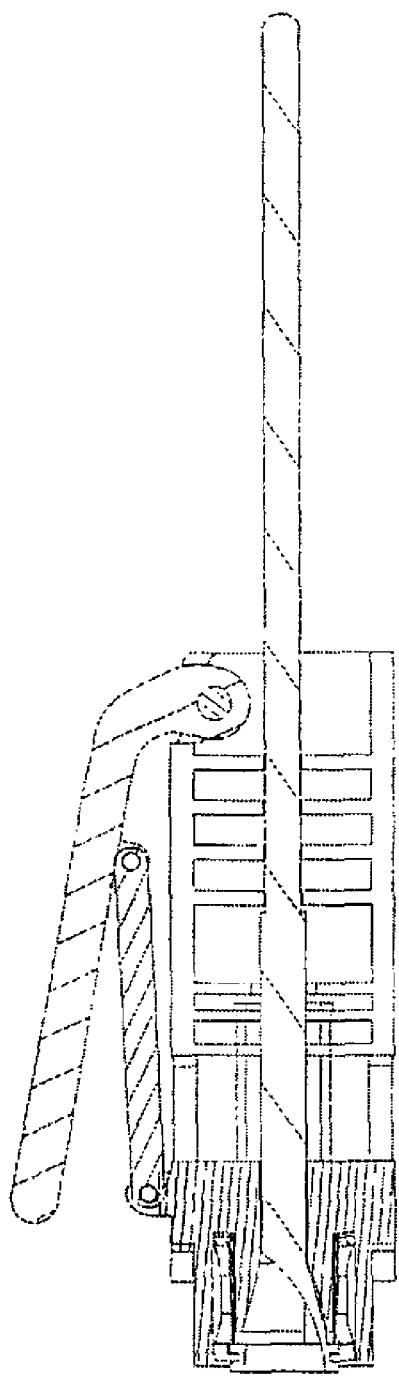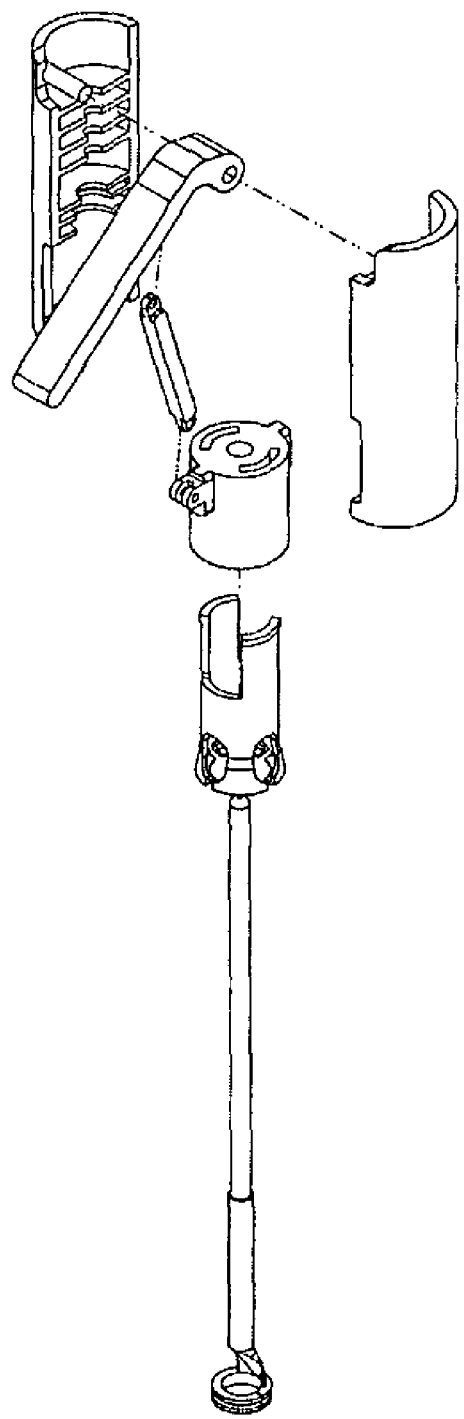
FIG 19
FIG 20

ATRAUMATIC CIRCUMCISION DEVICE AND METHOD TO USE SAME

CROSS REFERENCE TO RELATED APPLICATIONS

The present application claims benefit of U.S. Provisional Application Ser. No. 60/583,259, entitled "ATRAUMATIC CIRCUMCISION RING AND METHOD in" filed on Jun. 25, 2004, which is incorporated herein by reference.

FIELD OF THE INVENTION

The present invention is related generally to the field of circumcision, and more particularly to a method and device for neonatal circumcision enabling surgical removal of the excess foreskin or prepuce from the neonatal penis by a non-traumatic approach, eliminating the need for the traditional dorsal slit.

BACKGROUND OF THE INVENTION

Newborn circumcision is the most commonly performed surgical procedure in the United States with over 1 million circumcisions performed annually. Circumcisions have been performed for centuries for both religious and medical reasons. Various instruments have been developed to help facilitate removal of the foreskin from the penis. These instruments were intended to provide some level of hemostasis to help control bleeding, to provide a uniform cutting surface, and to protect the underlying glans penis from trauma associated with the procedure. Of these devices, three are commonly used for neonatal circumcision in the United States: U.S. Pat. No. 119,180 ('180) by A. A. Goldstein, U.S. Pat. No. 2,747,576 ('576) by H. Bronstein, and U.S. Pat. No. 2,272,072 ('072) by C. J. Ross and U.S. Pat. No. 3,056,407 ('407) by D. H. Kariher et al.

One shortcoming of all the prior art is that a dorsal slit in the foreskin is required. In a neonate, the opening of the foreskin at the tip of the penis is small and tight. A dorsal slit is made to free adhesions or separate the foreskin from the penis, allow enough room to accommodate a cutting surface, and to facilitate alignment of a cutting tool. This procedure causes a traumatic incision to be made on the dorsal surface of the foreskin, perpendicular to and unrelated to the final incision. In order to create the dorsal slit, considerable trauma is exerted to the foreskin and to the neonate.

In order to initiate the dorsal slit, it is necessary to grasp the foreskin. In practice, this is routinely done with two hemostats that are used to clamp and crush the distal foreskin at the ten o'clock position and the two o'clock position. By clamping and therefore crushing the foreskin, the surgeon is able to apply counter traction with one hand holding both instruments, while the surgeon uses the free hand to manipulate a third, straight hemostat to probe under the foreskin and then crush along the dorsal aspect. Scissors are used to cut the dorsal slit where the tissue was crushed. In order to create the dorsal slit, the foreskin of the newborn infant is unnecessarily crushed multiple times and cut.

Studies published by the American Academy of Pediatrics state that a majority of circumcisions are done without any form of anesthesia. The dorsal slit incision accounts for a significant amount of the pain and trauma associated with a circumcision. In addition, the dorsal slit can be a source for significant bleeding and possible infection. Additionally, the Food and Drug Administration (FDA) regularly reports cases where when attempting to perform the dorsal slit the surgeon inadvertently inserts the tip of the scissors into the urethral meatus and cuts not only through the foreskin but the glans penis itself.

The most commonly used neonatal circumcision clamp is described in U.S. Pat. No. 119,180 ('180) by A. A. Goldstein (referred to herein as the Gomco). It consists of a metallic bell that is used to cover the glans or head of the penis to provide protection. After the dorsal slit is made as described above, the foreskin is pulled over the bell and the bell is advanced upward through a hole that serves as a clamping surface. A fulcrum and a screw nut are used to apply a force between the clamp and the bell, which crushes the foreskin and serves to help control bleeding during the incision. One of the shortcomings of the Gomco is the difficulty to pull the foreskin up through the clamp because of the small hole and the size of the clamp. It is a common practice for surgeons using the Gomco to use a common safety pin to pierce the foreskin of the penis on either side of the dorsal slit to hold the foreskin together and to facilitate pulling the foreskin into the clamp. Piercing the foreskin twice with a sharp, large needle generates unnecessary pain and increases the possibility of bleeding and traumatic complications. Yet another shortcoming of the Gomco is that the bell is separate from the clamp making it possible to use the wrong size bell with the wrong size clamp. Traumatic complications, including penile amputations, have been caused because of this mismatch of bell and clamp. Furthermore, it is awkward to manipulate the large clamp and to attempt to pull the foreskin through the small bell opening while engaging the clamping mechanism. Lastly, the final incision is made with the free hand of the surgeon with a conventional scalpel attempting to cut around the bell. This procedure imposes a possibility of inadvertent placement of the scalpel in the wrong position with associated catastrophic outcomes, such as penile amputation.

Another commonly used circumcision device is described in U.S. Pat. No. 2,272,072 by Ross and U.S. Pat. No. 3,056,407 by Kariher et al. (referred to herein as the Plastibell), which also requires the traumatic dorsal slit. The Plastibell employs a plastic bell that is tied off with a string in a form of tourniquet. The remaining foreskin is trimmed with scissors. The plastic handle of the bell is broken off and the plastic bell stays in place until the foreskin necrosis and falls off. The most reported complication of the Plastibell is increased infections due to the foreign body nature of the plastic bell, string, and necrotic tissue. Many parents object to this method, because they do not want to have to worry about the plastic bell that stays in place for up to 5 days following the circumcision. Another shortcoming is that the string can be cut inadvertently by the surgeon performing the circumcision causing excessive bleeding. The string can also be tied with insufficient applied pressure to prevent bleeding. As with the Gomco, the chance for damage to the urethral opening of the glans is possible because the surgeon makes the incision with scissors. Lastly, it is very difficult and awkward to simultaneously hold the plastic bell in place, keep the foreskin together, and tie a knot in the string at the precise location on the plastic bell.

Yet another circumcision device is described in U.S. Pat. No. 2,747,576 ('576) by H. Bronstein (referred to herein as the Mogen clamp). The Mogan clamp is used less frequently because it is difficult to ensure that excessive foreskin or the head of the penis has not been inadvertently pulled up into the clamp. If the head of the penis is inadvertently pulled up into the clamp, the resulting clamping and incision causes an amputation of the tip of the penis. The FDA has issued several warnings regarding this shortcoming of the Mogen clamp. Furthermore, the cosmetic outcome is often that the remaining foreskin is lopsided and asymmetric because the incision is made in a linear direction and the underlying tissue has a circumferential orientation.

In August of 2000, the FDA released a cautionary statement regarding the Gomco and Mogen type clamps. The FDA reported receiving 105 reports of injuries involving circumcision clamps between the months of July 1996 and January 2000 or approximately 30 injuries per year. Assuming a similar injury rate for the preceding 54 years, when these devices were initially introduced, they have likely accounted for well over 1600 traumatic outcomes. Those incidents reported by the FDA included lacerations, hemorrhages, penile amputations, and urethral damage.

U.S. Pat. No. 3,072,126 by P. M. Fenton ('126) discloses the use of an axial circular cutting means to apply hemostasis compression to the foreskin as well as to cut the foreskin. The axial compression force applied by the circular cutting means to crush the foreskin invariably stretches and deforms the foreskin. As the circular cutting means is engaged, the foreskin is frequently and inappropriately pushed down over the bell or tube making it difficult to predict the length of foreskin to be removed. Since the same surface is used to cut the foreskin as well as to create the hemostatic crush to the foreskin, it would be difficult to ensure that the foreskin is not inadvertently cut prior to the application of enough compressive pressure to achieve hemostasis leaving the possibility of dangerous bleeding complications. Further, '126 requires use of a bell or tube to shield the glans, necessitating the inherent need for a dorsal slit to be made in the foreskin to facilitate the placement of the foreskin on to the bell or tube.

U.S. Pat. No. 3,473,533 by J. C. Freda ('533) discloses the use of an axial circular cutting means to cut the foreskin after an axially applied force creates a compressive force for hemostasis. The axial compression force to crush the foreskin invariably stretches and deforms the foreskin as the clamping member is applied. As the clamping member is engaged, the foreskin is frequently inappropriately pushed down over the bell or tube making it difficult to predict the length of foreskin to be removed. The incision to the foreskin is made independent of the crush which leaves open the dangerous possibility that an operator can inadvertently administer the cut without having first clamped the foreskin to create hemostasis. Further, '533 requires use of a bell or tube to shield the glans, necessitating the inherent need for a dorsal slit to be made in the foreskin to facilitate the placement of the foreskin on to the bell or tube.

A particular shortcoming shared by the prior art references is that none disclose a means to prevent the possibility of mismatched parts. The possibility of mismatched equipment or the use of a small shield with a large clamp has caused dangerous catastrophic outcomes as regularly reported by the FDA. These injuries are severe and include lacerations and penile amputations.

SUMMARY OF THE INVENTION

The present invention generally includes two cooperating components: a ring component and a clamping-cutting device. One embodiment of the ring component includes an open circular ring mounted to one end of a shaft. One embodiment of the clamping-cutting device includes a plurality of retractable arms operably connected to at least one movable lever arm. The clamping-cutting device also includes a cutting device (such as a circular blade) disposed within the clamping-cutting device, which is also operably connected to a lever arm. The shaft of the ring component may include a notch in a predetermined location to engage the clamping-cutting device to ensure precise positioning of the clamping-cutting device in relation to the open circular ring. The open circular ring may also include a circumferential groove along the outer surface of the open circular ring adapted to receive the edges of the retractable arms.

In operation, the ring component is manipulated between the foreskin and the penis and positioned just above the glans of the penis. The open ring allows insertion of the ring component into the foreskin without making a dorsal slit. This provides the placement of a clamping and cutting surface within the foreskin without making the unnecessary and traumatic dorsal slit. Once the open ring is placed within the foreskin without making a dorsal slit, the clamping-cutting device is placed onto the shaft of the ring component. The clamping-cutting device is then activated by moving the lever arm from the open to closed position. As the lever arm is moved downward or toward the closed position, the clamping-cutting device is moved over the plurality of retractable arms causing the arms to move radially inward to the closed position exerting a lateral, symmetric clamping force to the ring that serves to crush the foreskin. By exerting a lateral, symmetrical force, no manipulation or deformation of the foreskin has to occur to get it into the clamp. The ring is positioned within the foreskin and remains in that location until the lateral clamping force is applied. There is no need to pull or manipulate the foreskin to get it into the clamp. The clamp is delivered laterally and symmetrically to the foreskin and ring so there is no deformation to the foreskin prior to it being crushed, ensuring a more precise, reproducible, and predictable circumcision. In the closed position, the plurality of retractable arms close on to and engage the open circular ring, thereby closing the ring and crushing or clamping the foreskin against the now closed circular ring. At the moment the crush occurs, the foreskin remains in its anatomically correct position, improving the likelihood the physician can accurately determine the correct amount of foreskin to remove. Continued movement of the lever arm advances the cutting device towards the circular ring that cuts the foreskin clamped between the retractable arms and the circular ring.

One aspect of the present invention adapts a cutting device (such as a blade) to an actuator such that the cutting device translates parallel with the shaft of the penis when cutting the foreskin. The mechanical actuation of the cutting device provides an improvement in the control of the position of the cutting device relative to the shaft of the penis. The cutting device preferably translates along the common axis of the actuator which in turn translates along the common axis of the shaft of the ring component. The shaft of the ring component facilitates translation of the clamping-cutting device along the common axis providing control of the positioning and alignment of the cutting device with the compression and cutting surface of the ring component. The position of the shaft in relation to the compression and cutting surface is fixed such that the cutting device can only reach the exact location of the cutting surface, protecting surrounding tissue and eliminating any chance of inadvertent damage to the penis from the cutting blade. The blade is an integral part of the device, the incision can not be made until the housing has closed the retractable arms ensuring adequate clamping and crushing. The path of the blade is precisely controlled by the device itself, not the operator, ensuring the incision is made in the precise location, independent of the operator. The design of the present invention essentially eliminates the possibility of making an incision without having adequately crushed the foreskin. With this device, the timing of the crush and cut is precisely controlled, the incision can not occur without first crushing the foreskin.

Another aspect of the present invention is that the blade is contained and protected within the device itself, essentially eliminating the chance of inadvertent trauma to surrounding structures.

Another aspect of the present invention is that the internal shape of the opening of the clamping-cutting device can be made such that it can only mate with an appropriate ring. Anatomic variation requires devices of different size. This requires different size housings and different size rings. In order to completely eliminate the chance of using mismatched parts, the housing and ring will be uniquely mated, so that only the exact housing can be used with a particular sized ring. This mechanical specification will eliminate any chance of a user inadvertently using the wrong size ring with the wrong size clamping-cutting device. The design of this invention eliminates the possibility of mismatched parts and their potential catastrophic outcomes.

Another aspect of the present invention is that the open ring can be made to interact with the clamping-cutting device such that a mechanical stop can be used to control when and how the levers are activated. By using a mechanical stop, the two parts can be designed such that the lever arms can not be activated unless the clamping-cutting device is positioned in the exact position on the ring that inhibits the mechanical stop. This type of interaction can ensure that the clamping-cutting device can only be placed on the ring when in the open position, and the lever arms can only be activated when the clamping-cutting device is in the exact position on the ring. Furthermore, the design makes it impossible to move the housing once the lever arms have been activated, eliminating the chance of the operator pulling off the housing prior to completion of the crushing and the incision. The design ensures that the only way the operator can put the clamping-cutting device on the shaft of the ring is in the open position, eliminating the chance of the operator erroneously putting the clamping-cutting device on in the closed position. Furthermore, the design eliminates the chance of the operator activating the lever arms before the clamping-cutting device is in the exact location. It can also eliminate the chance of the clamping-cutting device moving at all along the shaft once the lever arms have been activated. The mechanical control of these important procedural elements ensures a reproducible, risk free circumcision, independent of the operator.

It is an object of the present invention to provide a device to easily perform newborn circumcision, shorten the operation time, produce reliable and consistent outcomes, and substantially eliminate the risk of human error and catastrophic outcomes.

It is a further object of the present invention to provide a device to perform neonatal circumcision that eliminates the need for the traditional dorsal crush and slit, thereby minimizing bleeding and significantly reducing the trauma and pain associated with the procedure.

It is a further object of the present invention to provide a device that delivers a lateral, symmetrical clamping force to the foreskin and the ring thereby eliminating the need to pull or manipulate the foreskin to position it in the clamping means.

It is a further object of the present invention to provide a device that facilitates the use of a circular cutting device that is delivered longitudinally to the shaft of the penis and performs a single circumferential and uniform incision.

It is a further object of the present invention to provide a device that integrates and encloses the circular blade within the device such that the device itself provides precise control over the delivery of the cutting surface while protecting the patient and user from inadvertent injury, essentially eliminating the chance of user error and catastrophic complications.

It is a further object of the present invention to provide a device that adapts a mechanical means to control the crushing of the foreskin and the delivery of the blade, ensuring that the incision can only be made after the foreskin has been sufficiently crushed.

It is a further object of the present invention to provide a mechanical means that completely eliminates the chance of mismatching different sized parts, eliminating the chance of a ring component being used with the wrong sized crushing-cutting device.

It is a further object of the present invention to use a lever arm with semicircular gears and a gear track to activate device.

It is a further object of the present invention to have the ability to manufacture each of the non-cutting surface parts out of plastic materials allowing the device to be disposable or recyclable for one time use, eliminating the need for autoclaving, reducing the risk of mismatched parts, and reducing the risks associated with using worn or damaged parts.

It is a further object of the present invention for the various sized parts to be made in differing colors based on size to assist users in identifying appropriate parts and appropriate sizes, expediting the procedure, and further avoiding the chance of mismatched parts.

It is a further object of the present invention to incorporate a mechanical means or lever locking system that ensures the levers that activate the device can only be activated when precise alignment of the ring and the clamping-cutting device has been achieved. And such mechanical means ensures the position of ring and clamping-cutting device is maintained throughout the actuation of the device.

It is a further object of the present invention to generate an audible sound when the lever arms have been successfully actuated to inform the operator that the crushing and cutting actions have been completed.

For a better understanding of the present invention, together with other and further objects thereof, reference is made to the accompanying drawings and detailed description.

BRIEF DESCRIPTION OF THE DRAWINGS

The present invention is illustratively shown and described in reference to the accompanying drawings, in which:

FIGS. 10, 11, and 12 are cross sectional views of various embodiments of the present invention illustrating insertion of various sized clamp-cutting surface apparatus into a clamping-cutting device FIGS. 13 and 14 are pictorial views of an alternative embodiment of the present invention;

FIG. 19 is a cross section views of yet another alternative embodiment of the present invention; and FIG. 20 is an exploded view of the alternative embodiment of FIG. 19.

DETAILED DESCRIPTION OF THE INVENTION

Figure 1:
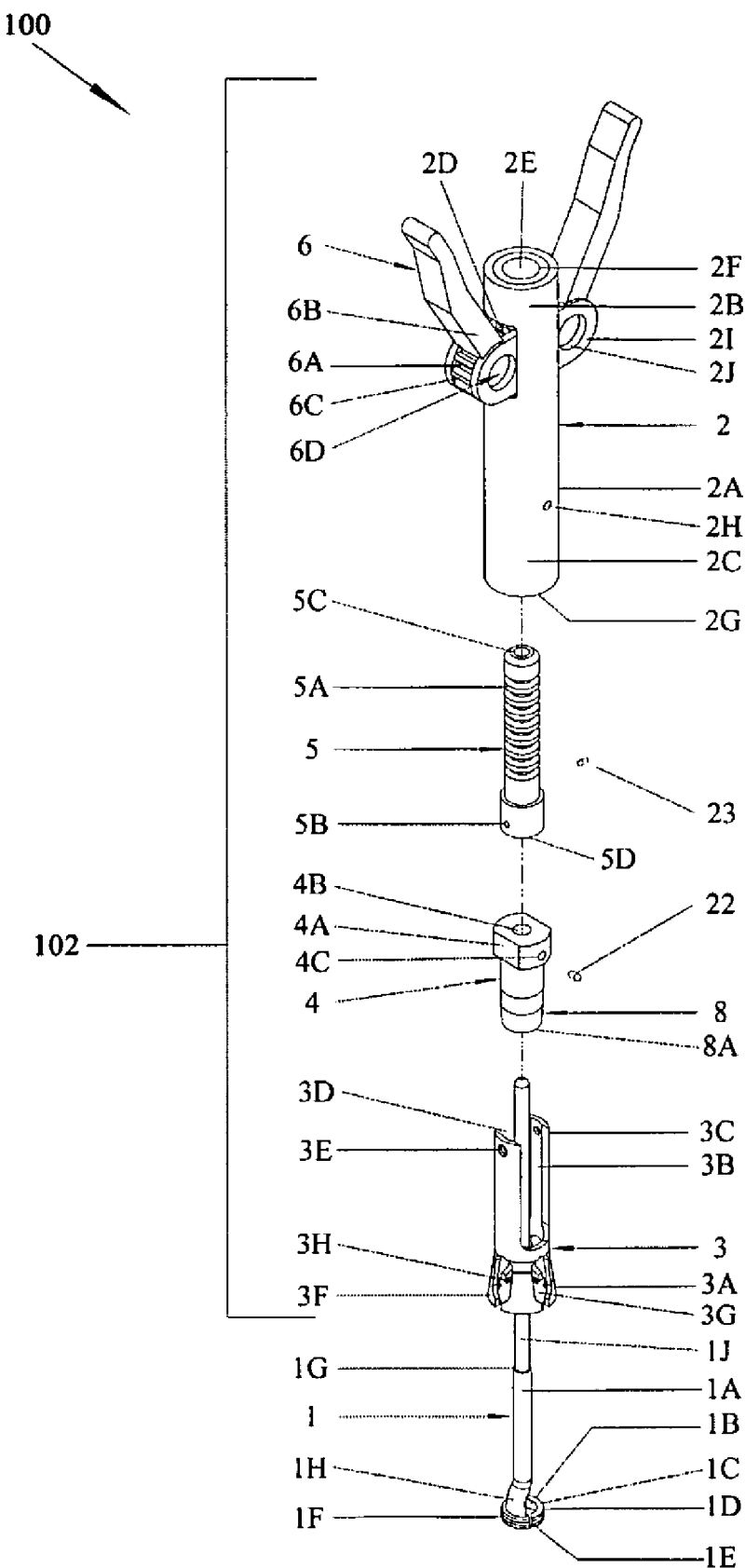
FIG. 1 is an exploded view of the present invention.
Figure 2:
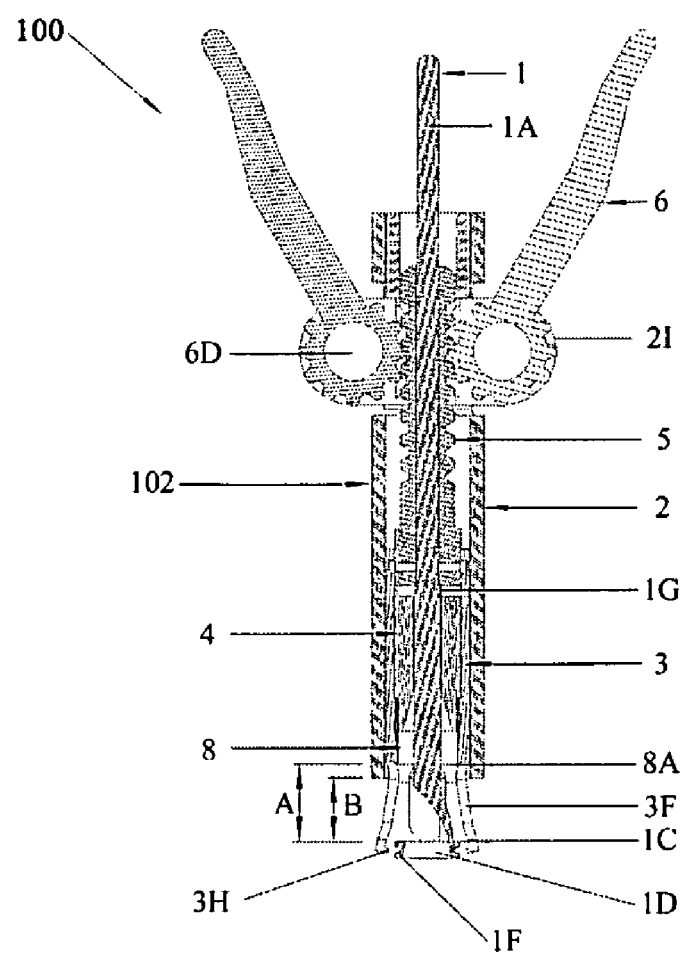
FIG. 2 is a cross-section of the present invention of FIG. 1 in the opened or relaxed position.
Figure 3:
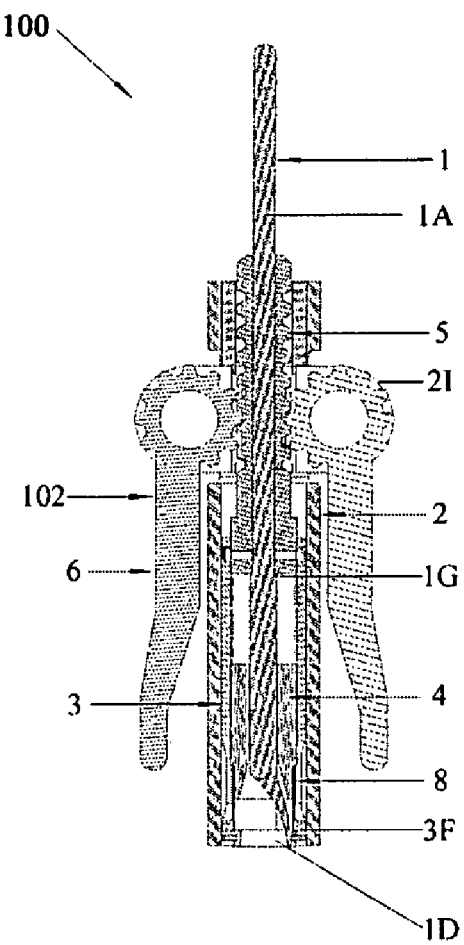
FIG. 3 is a cross-section of the present invention of FIG. 1 in the closed or engaged position.

One aspect of the present invention 100, illustrated in FIGS. 1, 2, and 3, includes ring component 1 and clamping-cutting device 102. Clamping-cutting device 102 includes operably connected housing 2, clamping member 3 with retractable arms 3F, blade holder 4 with integral blade 8, gear track 5, and two lever arms 6. Clamping member 3 is operably connected to lever arms 6 such that when lever arms 6 are actuated up retractable arms 3F are positioned out of clamping-cutting device 102 to the opened or resting position (FIG. 2) or when lever arms 6 are actuated down the clamping-cutting device 102 traverses over the clamping member 3 to the closed or engaged position (FIG. 3).

In the open position (FIG. 2), the ring component 1 is free to move into and out of clamping-cutting device 102. As lever arms 6 move downward to the closed position (FIG. 3), retractable arms 3F of clamping member 3 radially close and apply substantially even circumferential pressure to open ring 1D of the ring component 1 to firmly close the ring 1D and hold the ring component 1 in place as the housing 2 of the clamping-cutting surface 102 is advanced over the retractable arms 3F. In the clamped configuration, the ring component 1 and the clamping-cutting device 102 act as a single, integral component controlled by the actuation of level arms 6. Downward progress of crushing-cutting component 102, a distance designated B, advances housing 2 over retractable arms 3F such that the clamping operation is fully activated or engaged. At the moment the housing 2 has been advanced the distance B and the crush has been completed, the blade has traveled the same distance B and is positioned above the ring and cutting surface. It is not until the lever arm 3 has been further actuated and the housing 2 and blade 8 have been advanced further down clamping member 3 a distance designated A that the cutting edge 8A is brought into contact with the cutting surface 1C of ring 1D thereby incising the foreskin positioned between the cutting edge 8A and the cutting surface 1C. During further advancement of housing 2 over the retractable arms the crushing force of retractable arms 3F are maintained by the inner diameter of the housing 2. The timing of the crush and cut is controlled by distances A and B. These distances are sufficiently different to ensure that the clamping action occurs prior to the incision. And more importantly, that an incision can not possibly be made without first activating and maintaining the clamping action. Downward progress A of crushing-cutting component 102 stops when the cutting edge 8A of blade 8 contacts the top or cutting surface 1C of ring 1D of the ring component 1. The sequence of the crush and cut is controlled by the device itself when the operator actuates the lever arms downward fully in one single motion. As lever arms 6 are actuated, the present invention clamps the foreskin radially to create a substantially symmetrical and even circumferential hemostasis at the axial position and at the same time as the motion continues and only after the crush has occurred, delivers the cutting edge of blade 8 to the cutting surface 1C of the ring 1D completing the incision slightly above where the clamping member 3 crushed the foreskin and achieved the hemostasis affect. The incision to the foreskin is made while the foreskin is within housing 2 and can be out of the direct line of sight of the operator if housing 2 is made of a non-transparent material or colored.

Housing 2 is generally cylindrical, hollow, and vertically longitudinal having an top portion 2B and a bottom portion 2C. Housing 2 includes top portion 2B, bottom portion 2C, opposing slots 2D, through bore 2E, top opening 2F, bottom opening 2G, assembly hole 2H, and two pairs of projections 2I. Bore 2E includes a sufficiently sized inner surface and length to receive therein clamping member 3, blade holder 4, gear track 5, and ring component 1.

Two lever arms 6 are pivotally joined to top portion 2B about a pivotal axis. Each lever arm 6 has a predetermined length and width sufficient to sustain the forces of clamping and cutting. Semi-circular gears 6A are adapted to the distal end 6B of each lever arm 6 and a handle at the other end. Lever arms 6 are positioned on opposite sides of top portion 2B of housing 2 and positioned such that a portion of semi-circular gear 6A extends through a slot 2D in housing 2 so as to engage gear track 5 within housing 2. Each semi-circular gear 6A includes a plurality of gear teeth 6C. Width of lever arms 6 are sized to fit between pair of projections 2I and are pivotally attached to projections 2I by a conventional joining device (not shown) such as bolt/nut or bushing or pressed fit pin connection. Each projection 2I may include hole 2J to receive the conventional joining device. Each semi-circular gear 6A may include a through bore 6D to receive the conventional joining means therethrough pivotally connecting each lever arm 6 and projection 2I with one conventional joining means. Alternatively, two conventional joining means can be inserted through each projection 2I into semi-circular gears 6A, either with or without a through bore, to form the pivotal connection. Projections 2I act as a pivotal axis for lever arms 6 and allow lever arms 6 to rotate or pivot about an axis. Pivotal movement of lever arms 6 causes rotation of semi-circular gears 6A to impart reciprocating movement to gear track 5. Semi-circular gears 6A have a diameter that is sufficient to linearly move housing 2 up and down over retractable arms 3F.

Bottom opening 2G of bottom portion 2C of housing 2 has an inside diameter that is made to accommodate the top portion of clamping member 3. As housing 2 is advanced down over clamping member 3, the inside diameter of housing 2 causes retractable arms 3F of clamping member 3 to radially close, such that when housing 2 is advance completely over clamping member 3, retractable arms 3F are closed and in a position to engage open ring 1D and exert a significant compressive force on grooved outer surface 1F of open ring 1D.

Gear track 5 includes a plurality of gear teeth 5A evenly spaced along the length of gear track 5. Gear track 5 further includes through radial hole 5B for connecting clamping member 3 to gear track 5 (disclosed in detail below). Gear track 5 is initially positioned within top portion 2B of housing 2 and is capable of axial movement within housing 2 in either longitudinal direction. Gear teeth 5A of gear track 5 cooperate with gear teeth 6C of semi-circular gears 6A to translate gear track 5 axially within bore 2E of housing 2. Gear track 5 has a vertical passageway 5C extending through its axial center that is sized to receive only the narrow portion of shaft 1A of ring component 1. By accommodating only the narrow part of shaft 1A, bottom face 5D contacts or rests on notch, ledge or shoulder 1G of shaft 1A, and therefore aligns the clamping-cutting device 102 with ring component 1 and open ring 1D (discussed in detail below). Shoulder 1G can be formed by shaft 1A having two sections with different diameters: an upper section 1J having a diameter smaller than diameter of 5C and a lower section 1A having a diameter larger than diameter of 5C. Gear track 5 is freely rotatable about its axis and gear teeth 5A extend circumferentially around gear track 5. The contact at any given time between gear teeth 6C of semi-circular gear 6A and gear teeth 5A on gear track 5 is limited to a single tooth and preferably a single point contact.

Blade holder 4 includes circular blade 8 and blade support 4A. Circular blade 8 and blade support 4A are connected by conventional means including, for example, snap fit, press or interference fit, cooperating male/female threaded members, screw, bolt, pin, weld, or adhesive. Blade support 4A includes longitudinal through bore 4B (disclosed in detail below). Blade support 4A may include retention hole 4C to connect blade holder 4 to housing 2 with, for example pin 22. Further, blade holder 4 has an outer diameter less then that of the inside diameter of clamping member 3 such that blade holder 4 can move freely longitudinally within clamping member 3. At the location of slot 3D in clamping member 3, blade holder 4 is affixed to housing 2 and moves simultaneously with housing 2. Blade holder 4 and housing 2 are attached together and move as one component. The attachment point occurs at the location of slot 3D such that housing 2 and blade holder 4 can move independently of clamping member 3.

Clamping member 3 is generally a hollow cylindrical member with lower end 3A and upper end 3C. Clamping member 3 is freely moveable within the lower part of housing 2. The hollow center of clamping member 3 allows for the positioning and passing therethrough of blade holder 4. Clamping member 3 includes a plurality of retractable arms 3F at lower end 3A. Upper end 3C is defined by two extensions 3B positioned on opposite sides of the cylinder at upper end 3C. Pair of extensions 3B are adapted to form slot 3D. Slot 3D is sized to receive blade holder 4 and gear track 5. Each extension 3B includes retention hole 3E for connecting clamping member 3 to gear track 5 with, for example, pin 23. Slot 3D extends longitudinally along the cylinder and allows for fixation of blade holder 4 to housing 2 (discussed in detail below) without interfering with clamping member 3 ability to traverse within housing 2. Once clamping member 3 is fixedly attached to gear track 5, gear track 5 drives housing 2 up and down over clamping member 3, thereby opening and closing retractable arms 3F.

As discussed above, lower end 3A of clamping member 3 includes of a plurality of circumferentially evenly spaced, downwardly facing, outwardly tapered, flexible retractable arms 3F. Retractable arms 3F can be made of elastic material, such as plastic, metal, graphite, or other polymer, that retains its spring-like characteristics. The ends of retractable arms 3F form an opening 3G adapted to engage grooved outer surface 1F of open ring 1D. When the present invention is in the opened or relaxed position, opening 3G is larger then the outer diameter of open ring 1D. Retractable arms 3F extend outwardly in a tapered manner allowing for an open position that allows for positioning of clamping member 3 over the outside diameter of the upper section 1J of shaft 1A. As housing 2 is advanced down over retractable arms 3F, the inside diameter of housing 2 engages the tapered edge of retractable arms 3F and results in the closure of retractable arms 3F. When retractable arms 3F are closed, the ends of retractable arms 3F define an opening 3G that is substantially the same diameter as the outer diameter of open ring 1D when gap 1E of open ring 1D is closed. Retractable arms 3F, when closed, cooperate with grooved outer surface 1F of open ring 1D to crush the foreskin for a hemostasis effect and hold open ring 1D in a secure, fixed position prior to the delivery of the axial force of blade 8 to the prepuce foreskin.

As discussed above, retractable arms 3F are fully extended or opened in the unrestrained condition, thereby forming the largest opening diameter 3G possible. As retractable arms 3F are drawn axially into, for example, housing 2, retractable arms 3F move radially inward, thereby reducing the diameter of opening 3G. Retractable arms 3F are adapted to engaged ring component 1, crush the foreskin, and restrain the movement of ring component 1. Each retractable arm 3F may include inward radial extension 3H, which is preferably curved to fit the contour of grooved outer surface 1F, to further enhance the hemostasis effect. Four retractable arms are illustrated, however, any number of arms are acceptable that achieve the desired results discussed in detail below.

One embodiment of the clamping-cutting device 102 can be assembled by aligning retention hole 3E of clamping member 3 with radial hole 5B of gear track 5. A conventional means such as a screw, bolt, or press-fit pin 23 is inserted through retention hole 3E and radial hole 5B of gear track 5, thereby connecting together clamping member 3 and gear track 5. Blade holder 4 is place within the assembled clamping member 3/gear track 5 and the entire assembly is positioned within through bore 2E of housing 2. Retention hole 4C of blade holder 4 is aligned with assembly hole 2H of housing 2. A conventional means such as a screw, bolt, or press-fit pin 22 is inserted through retention hole 4C of blade holder 4 and assembly hole 2H of housing 2, thereby connecting together housing 2 and blade holder 4. Each lever arm 6 is positioned between pair of projections 21. Semi-circular gears 6A are extended into housing 2A through slot 2D. Gear teeth 6C of semi-circular gears 6A are positioned to engage gears 5A of gear track 5. A conventional joining device is adapted to pivotally attach lever arm 6 to projection 21, thereby completing the assembly of clamping-cutting device 102.

Figure 4:
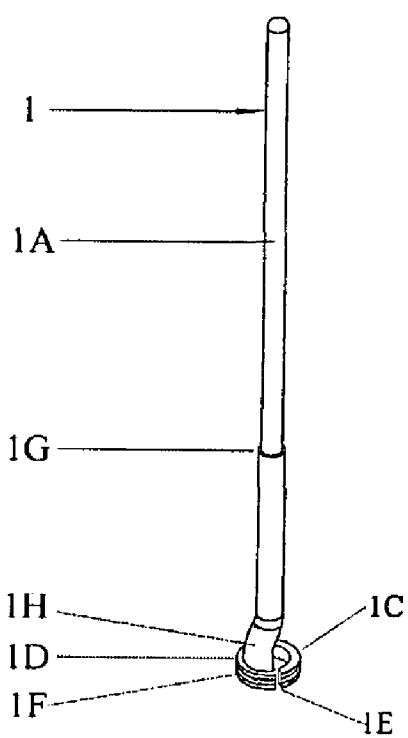
FIG. 4 is a pictorial view of one embodiment of the clamping-cutting surface apparatus of the present invention.
Figure 5:
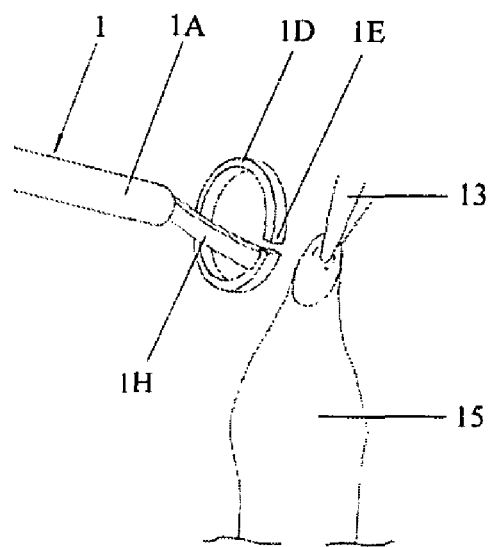
FIGS. 5, 6, 7, and 8 are pictorial views of the clamp-cutting apparatus being inserted into the foreskin of the neonatal penis.
Figure 6:
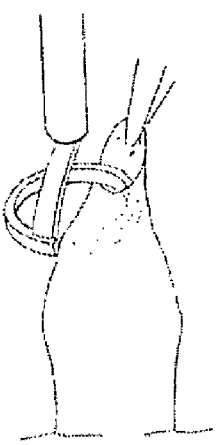
Figure 7:
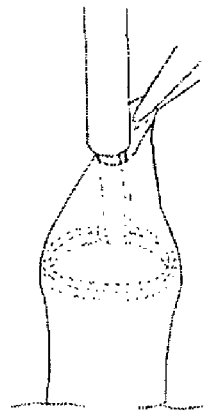
Figure 8:
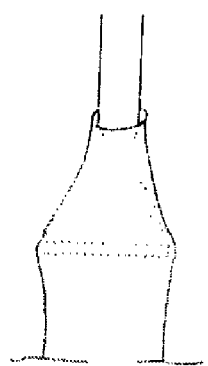

Now turning to FIG. 4, ring component 1 is generally a single piece of malleable, elastic material (such as plastic) with an open ring 1D mounted orthogonally to shaft 1A by curved member 1H, which allows manipulation of open ring 1D within the foreskin. Shaft 1 A includes a plurality of diameters to control the insertion of ring component 1 into clamping-cutting device 102. A shaft diameter change can be delineated by a notch or ledge or, as illustrated in FIG. 1, shoulder 1G that acts as a stop of ring component 1 into clamping-cutting device 102. Open ring 1D includes a cutting surface 1C on its top surface being adapted to act as a cutting surface when cutting edge 8A of blade 8 is pressed down against foreskin interposed between cutting surface 1C and cutting edge 8A. Open ring 1D may also include grooved outer surface 1F adapted to engage with inward radial extension 3H of retractable arm 3F to hold ring component in a stationary position relative to housing 2 during the clamping/cutting operation, such that the foreskin is trapped between the grooved outer surface 1F and the retractable arms 3F. Further, grooved outer surface 1F will interact with inward radial extension 3H to crush the foreskin against open ring 1D and contemporaneously hold ring component 1 in position while circular blade 8 is delivered to make the incision in the foreskin. Open ring 1D includes an opening or gap 1E large enough to allow the thickness of the foreskin to enter. The inner diameter of the open ring 1D is large enough to receive a predetermined sized glans and shield the glans or head of the penis from being clamped and/or cut.

FIGS. 5, 6, 7, and 8 demonstrate the insertion of open ring 1D into the neonatal foreskin 15. As discussed above, opening 1E allows entry of open ring 1D into foreskin 15. Foreskin 15 is held by an atraumatic forceps 13 while opening 1E is positioned to enter foreskin 15. With a pair of non-traumatic forceps, the foreskin is gently grasped and foreskin 15 is guided into the narrow gap 1E of open ring 1D. With a screw-like motion of shaft 1A of ring component 1, the open edge of open ring 1D is advanced in, down, and around the inner aspect of the foreskin. The opening or gap 1E in open ring 1D allows the open edge to be advanced into the foreskin with a smooth, non traumatic fluid screwing motion. Once open ring 1D is fully inserted and resides just beneath foreskin 15, it can be pushed down slowly toward the glans to free any adhesions. Inside foreskin 15, opening or gap 1E is closed by the elastic nature of the foreskin. The closed open ring 1D, inside the foreskin of the penis, residing just above the glans or tip of the penis, is then used as the compressive surface for any number of clamps, such as inward radial extension 3H, and its top surface acts as a combination glans shield and or cut surface for blade 8 as it cuts the foreskin.

Figure 9:
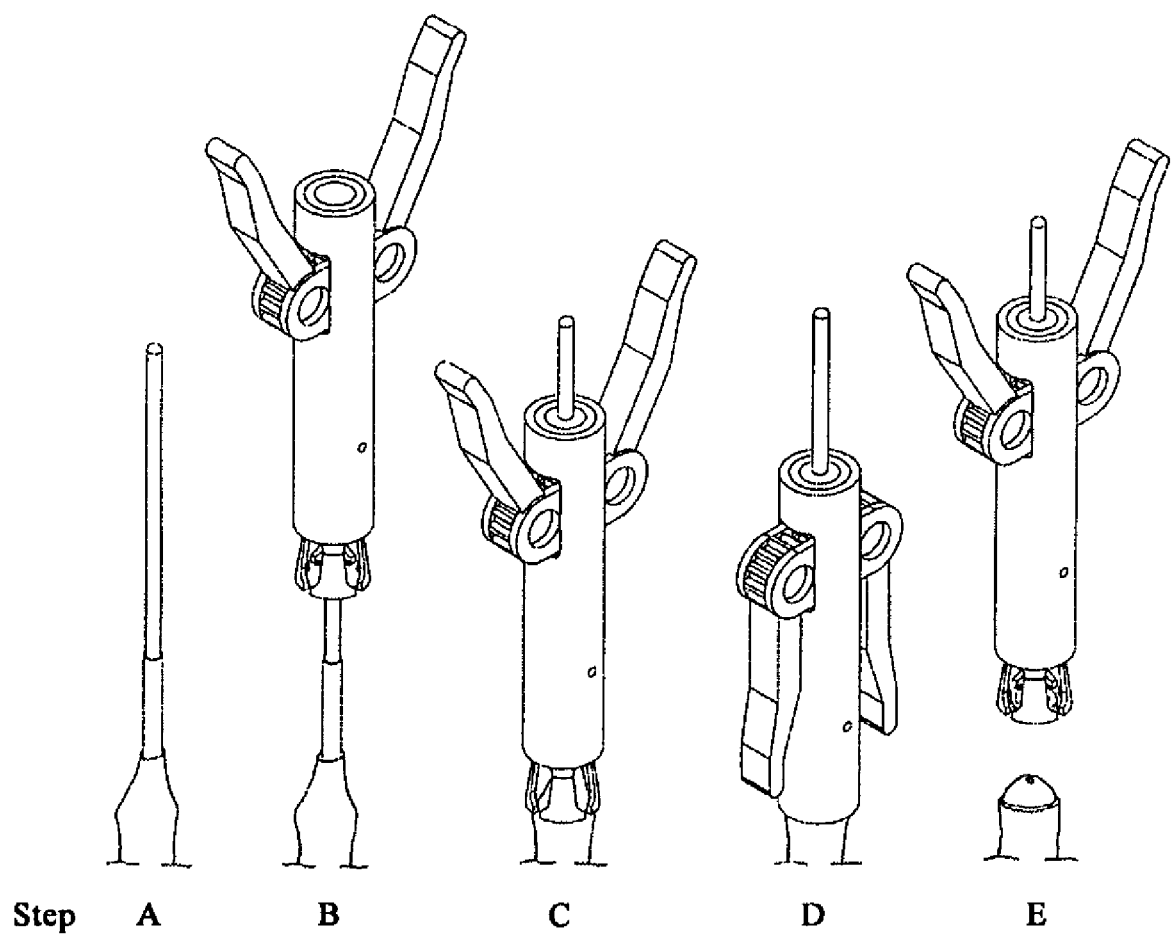
FIG. 9 are pictorial views illustrating use of the present invention.

FIG. 9 illustrates the method of using the present invention to perform a neonatal circumcision. Step A: Open ring 1D of ring component 1 is inserted into the foreskin of the penis, as discussed above. Step B: Clamping-cutting device 102 is set in the open position with lever arms 6 rotated up and retractable arms 3F extending fully through the bottom of housing 2. Step C: Clamping-cutting device 102 is inserted onto shaft 1A of ring component 1. Downward movement of clamping-cutting device 102 and housing 2 onto shaft 1A is stopped when shoulder 1G contacts bottom face 5D of gear track. Step D: Lever arms 6 are activated downward to advance housing 2 downward over retractable arms 3F causing the clamping force and delivering the circular blade to the foreskin. More specifically, semi-circular gears 6A of lever arms 6 engage with gear teeth 5A of gear track 5 of clamping-cutting device 102. Housing 2 moves downwardly over retractable arms 3F causing retractable arms 3F to radially close on to and to exert lateral compressive force against the foreskin. Retractable arms 3F exert sufficient lateral compressive force such that inward radial extensions 3H of retractable arms 3F forces the foreskin into grooved outer surface 1F of open ring 1D, thereby clamping the foreskin without any trauma or deformation between the ring component 1 and the clamping-cutting device 102. As housing 2 is advanced even further over the open ring 1D, blade 8 is delivered to the top surface of open ring 1D and creates the circular incision into the foreskin when open ring 1D is within housing 2. Using the top surface 1C of open ring 1D as the cutting surface that is held in place by the closed retractable arms 3F, blade 8 makes a single, clean, circumferential incision on top of the ring, removing the excess foreskin. The clamp is left in place for a period of time ensuring adequate crushing and hemostasis. Step E: Lever arms 6 are lifted upward and retractable arms 3F release ring component 1, lifting housing 2 of the clamping-cutting device 102 and lifting blade 8 back up into housing 2 and releasing open ring 1D. Shaft 1A with severed foreskin is removed from housing 2. All components of the present invention and byproducts of the operation are thrown away, thereby completing the circumcision.

FIGS. 10, 11, and 12 illustrate how the present invention eliminates the chance of mismatched parts. In FIG. 10, smaller ring component 16 is shown inside larger housing 17. The location of the shoulder 10 on the shaft of ring component 16 prevents shaft from being inserted all the way into the housing 17. With open ring extending below retractable arms, clamping-cutting surface apparatus 16 and housing 17 are not engaged and blade may not cut foreskin. Therefore, the use of a smaller ring component 16 with larger housing 17 is prevented.

FIG. 11 illustrates a proper fit between ring component 18 and housing 17. Ring component 18 is the appropriate size for the housing 17 and the retractable arms 9 are perfectly aligned with the open ring 14. Ring component 18 and housing 17 engage and blade cuts foreskin.

FIG. 12 illustrates how a larger ring component 19 interacts with a smaller housing 17. In this case, it is the diameter of the shaft of ring component 19 that prevents the shaft from being inserted into housing 17. On the shaft of ring component 19, the location of the shoulder and the diameter of the shaft make up two variables that are used together to completely eliminate the chance that a wrong size ring component could be used with a wrong size housing. Colored coded rings that match the appropriate size housing can be used to help users identify appropriate parts and appropriate sizes.

FIGS. 13 and 14 illustrate an alternative embodiment of the clamping-cutting device of the present invention having a lever-locking system to ensure more accurate deployment of lever arms 6. Lever arm 6 is in the up or open position aligning slot 21 in the pivotal axial shaft of the lever arm 6 that would allow lever arm 6 to be slid into position on the shaft 1. Because of slot 21, lever arm 6, in the position shown, can not be deployed. Lever arm 6 is jammed or blocked from rotating because of the shaft.

In FIG. 14, lever arm 6 has been moved down shaft 1 and is aligned with curved notch 20 in shaft 1. Curved notch 20 allows lever arm 6 to rotate to the down or closed position. The location of curved notch 21 in shaft 1 ensures that lever arms 6 can only be deployed when the clamping-cutting device 2 is in the precise location on shaft 1. Furthermore, once lever arm 6 is deployed, lever arm 6 can not move up or down on shaft 1 because it becomes locked in place as a result of the curved notch 21.

Figures 15, 16:
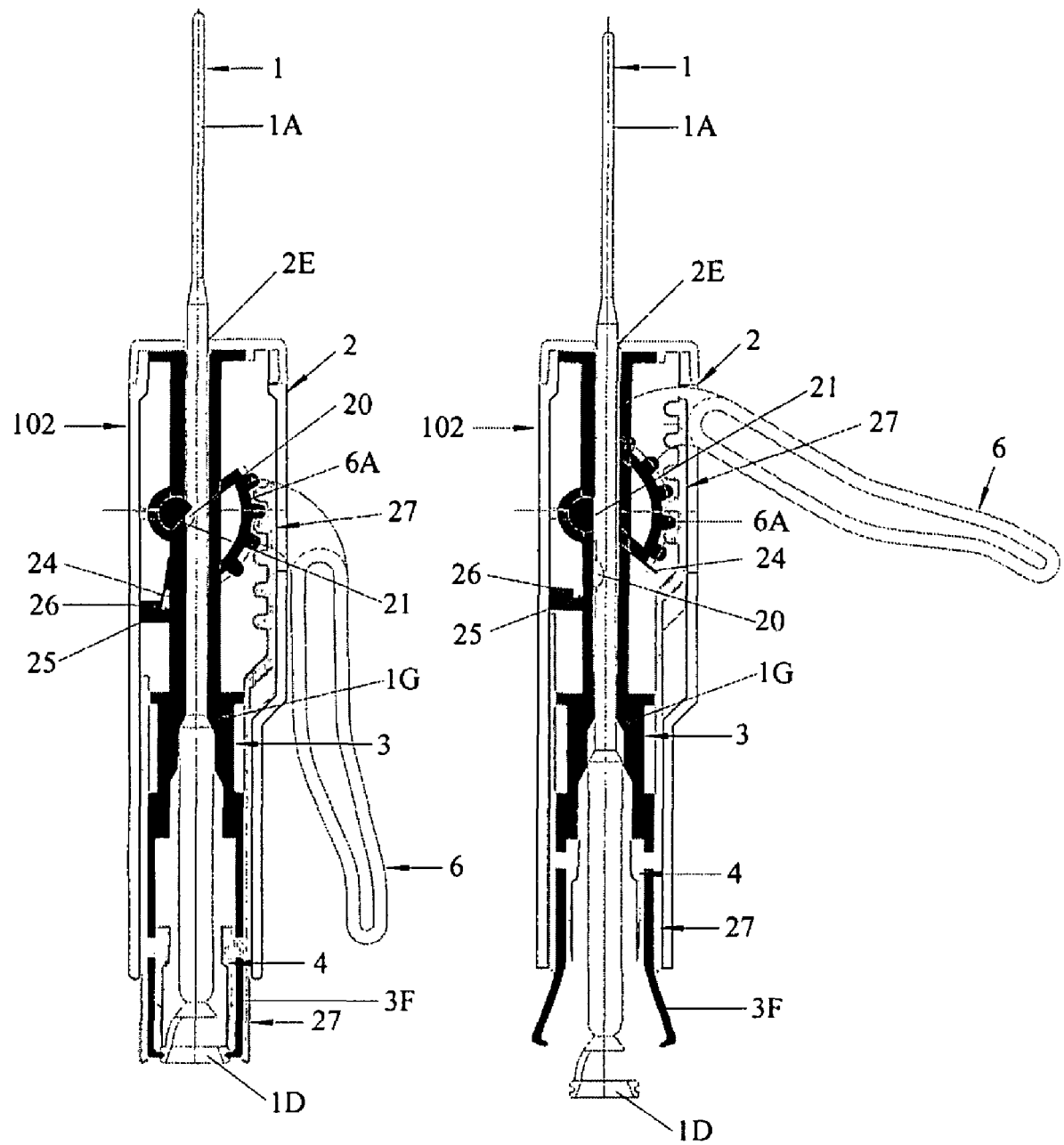
FIGS. 15 and 16 are cross section views of another alternative embodiment of the present invention.

FIGS. 15 and 16 illustrate yet another alternative embodiment of the clamping-cutting device of the present invention in the open and closed position. This embodiment incorporates a means to generate a clicking sound when the lever arm has moved a sufficient distance to ensure clamping and cutting. Elastic projection 24 of semicircular gear 6A makes contact with projection 25 of the clamping member 3. As the semicircular gear 6A rotates, elastic projection 24 is held by projection 25 until semicircular gear 6A rotates a sufficient amount that elastic projection 24 snaps free thereby striking surface 26 of the clamping member and making a distinct click. The position of the elastic projection 24 on the semicircular gear 6A is such that the clicking sound occurs when the lever arm 6 is in the fully closed or down position. The clicking sound provides an audible signal to the operator that the lever arm has been appropriately deployed and that the crushing and cutting is complete.

FIGS. 15 and 16 also demonstrate a clamping-cutting device that has a housing 2 that is fixed to clamping member 3. Once in position on ring component 1, the housing 2 of the clamping-cutting device 102 does not move. Activation of lever arm 6 and semicircular gears 6A causes rotation about an axis fixed to housing 2. Rotation of the semicircular gears 6A activates reciprocating movement of an internal cylindrical sleeve 27 that moves within housing 2 and can be advanced over the clamping member 3 to close retractable arms 3F. The internal sleeve 27 is fixedly attached to blade holder 4 allowing advancement of the sleeve 27 to deliver the blade holder 4 and the cutting surface to ring 1D of ring component 1. FIG. 16 demonstrates sleeve 27 and blade holder 4 in the up position, retracted into housing 2. FIG. 15 demonstrates sleeve 27 and blade holder 4 in the down position, extending below housing 2, closing retractable arms 3F and delivering the cutting surface to the top surface of the ring 1D.

FIG. 16 also demonstrates a clamping-cutting device that utilizes just one lever arm and demonstrates how the lever-locking system can be used. As shown if FIG. 16, the shaft 1A of the ring component 1 can only be inserted into the thru hole 2E of the housing 2 when the lever arm 6 is in the up position thereby aligning slot 21 vertically and allowing clearance for shaft 1A to traverse through thru hole 2E. Once the ring component 1 is inserted into thru hole 2E of housing 2, the notch 21 prevents rotation of the lever arms 6. FIG. 15 demonstrates how rotation of the lever arms can only be initiated when slot 20 of the ring component 1 is aligned with notch 21 allowing rotation of the lever arms and activation of the clamping-cutting device. At the precise location where notch 21 is aligned with slot 20, the ring component 1 is in perfect alignment with the clamping-cutting device 102. It is only when such precise alignment occurs that the operator is able to activate the clamping-cutting device.

Figure 17:
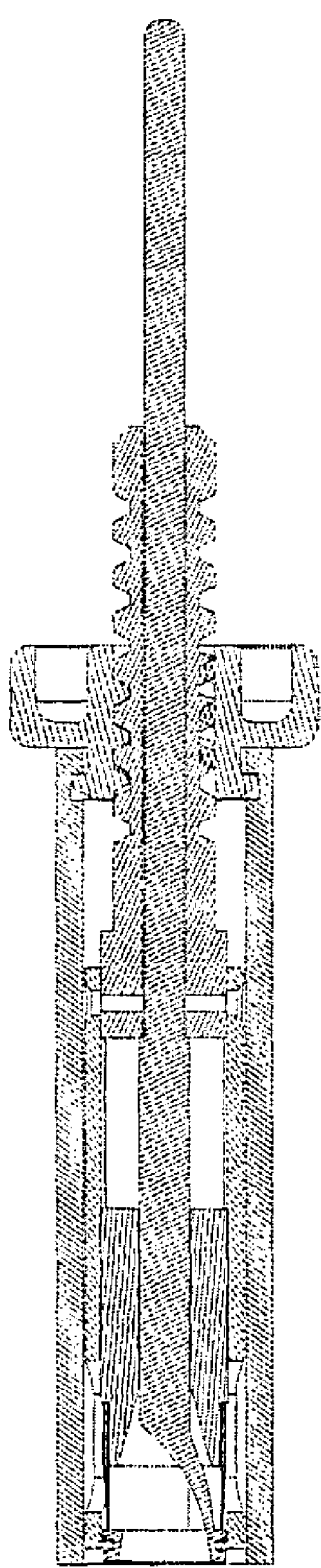
FIG. 17 is a cross section views of yet another alternative embodiment of the present invention.
Figure 18:
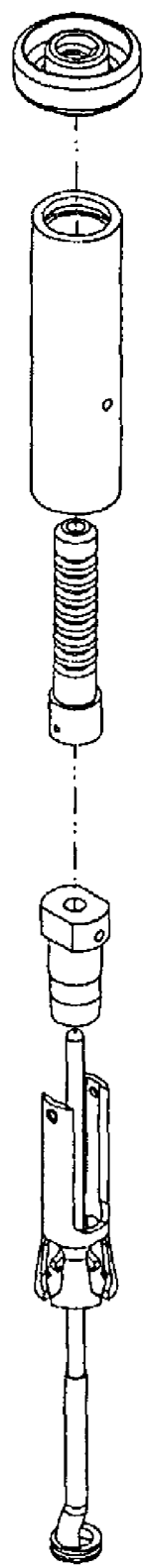
FIG. 18 is an exploded view of the alternative embodiment of FIG. 17.

FIGS. 17 and 18 illustrate other alternative embodiments of the clamping-cutting device of the present invention wherein a clamping-cutting device utilizes a threaded screw to advance the housing over the retractable arms.

FIGS. 19 and 20 illustrate yet other alternative embodiments of the clamping-cutting device of the present invention that uses one lever arm and a lining system.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A circumcision system for removing excess foreskin from the neonatal penis comprising: a housing having a through bore; a radial clamping device having a plurality of longitudinal clamping arms, at least a portion of said radial clamping device being disposed within said bore of said housing; a axial cutting device having axially oriented blade, said axial cutting device being fixedly attached to said housing within said bore, said axial cutting device having a cutting edge; a ring component having a clamping surface adapted to engage said plurality of longitudinal clamping arms and a cutting surface adapted to engage said axially oriented blade; an actuation mechanism being operably connected to said plurality of longitudinal clamping arms to radially translate said plurality of longitudinal clamping arms inward to clamp said ring component; and said actuation mechanism being operably connected to said axial cutting device to axially translate said cutting edge relative to said clamped ring component to cut the excess foreskin.

2. The circumcision system according to claim 1 further comprising a cutting delay mechanism defined by an axial distance between said cutting edge of said axially oriented blade and said cutting surface of said ring component.

3. The circumcision system according to claim 1 wherein said actuation mechanism comprises: at least one lever arm with a plurality of gear teeth disposed at its distal end, said at least one lever arm being pivotally connected to said housing, at least a portion of said plurality of gear teeth being disposed within said housing; a gear track with a plurality of gear teeth, said gear tracking being capable of axial translation within said housing; and said at least a portion of said plurality of gear teeth of said at least one lever arm capable of rotation engagement with said plurality of gear teeth of said gear track, whereby said gear track translates axially in either direction within said housing when said at least one lever arm is actuated upward or downward.

4. The circumcision system according to claim 1 wherein said ring component further comprises an opening sufficiently sized to allow thickness of the foreskin to pass therethrough.

5. The circumcision system according to claim 1 wherein said ring component further comprises a grooved outer surface adapted to engage said plurality of longitudinal clamping arms.

6. The circumcision system according to claim 1 wherein said ring component further comprises an inner diameter sufficiently sized to shield glans of the penis from injury.

7. The circumcision system according to claim 1 further comprising an audible device operably connected to said actuation mechanism to signal the operator that the clamping and cutting operations have been completed.

8. The circumcision system according to claim 1 wherein said cutting edge is a circular blade.

9. The circumcision system according to claim 1 wherein said radial clamping device, said axial cutting device, and said actuation mechanism are operably connected to said housing to form a clamping-cutting device.

10. The circumcision system according to claim 9 further comprising an locking system operably connected to said actuation mechanism to ensure precise alignment of said ring component with said clamping-cutting device has been achieved:

11. The circumcision system according to claim 9 wherein said ring component and said clamping-cutting device include size indicia for matching said ring component with the appropriately sized clamping-cutting device to avoid mismatched devices.

12. The circumcision system according to claim 9 wherein: said ring component further comprises a shaft attached to said ring component, said shaft having at least one obstruction disposed at a predetermined along its longitudinal length; and said clamping-cutting device further including an opposing obstruction to stop the relative axial translation of said shaft into said clamping-cutting device when said at least one obstruction contacts said opposing obstruction, whereby said ring component is juxtapositioned axially to said plurality of retractable arms when said ring component is matched with appropriately sized clamping-cutting device.

13. The circumcision system according to claim 1 wherein said ring component, said housing, said radial clamping device, said axial cutting device, and said actuation mechanism are made substantially of polymer material, whereby allowing said circumcision system to be disposable or recyclable and suitable for one time use.

* * * * *